United States Patent
Colombo et al.

(10) Patent No.: US 7,301,027 B2
(45) Date of Patent: Nov. 27, 2007

(54) PROCESS FOR THE PREPARATION OF IMIQUIMOD AND INTERMEDIATES THEREOF

(75) Inventors: Lino Colombo, Pavia (IT); Enrico Mariotti, Malonno (IT); Pietro Allegrini, San Donato Milanese (IT); Graziano Castaldi, Briona (IT)

(73) Assignee: Dipharma S.p.A., Mereto di Tomba (IT)

( * ) Notice: Subject to any disclaimer, the term of this patent is extended or adjusted under 35 U.S.C. 154(b) by 308 days.

(21) Appl. No.: 10/979,209

(22) Filed: Nov. 3, 2004

(65) Prior Publication Data
US 2005/0165236 A1    Jul. 28, 2005

(30) Foreign Application Priority Data
Nov. 4, 2003    (IT) ................... MI2003A2121

(51) Int. Cl.
*C07D 471/00*    (2006.01)

(52) U.S. Cl. ......................................................... 546/82

(58) Field of Classification Search .................... 546/82
See application file for complete search history.

(56) References Cited

FOREIGN PATENT DOCUMENTS

| EP | 0145340 A2 * | 11/1984 |
| EP | 145340 A2 * | 6/1985 |

OTHER PUBLICATIONS

Yoshioka et al., Chem.Pharm. Bull. 44(4), 709-714, 1996.*

* cited by examiner

Primary Examiner—D. Margaret Seaman
Assistant Examiner—Nizal S. Chandrakumar
(74) Attorney, Agent, or Firm—Young & Thompson

(57) ABSTRACT

Novel intermediates useful for the preparation of Imiquimod and a process for the preparation of Imiquimod with the intermediates.

6 Claims, No Drawings

PROCESS FOR THE PREPARATION OF IMIQUIMOD AND INTERMEDIATES THEREOF

FIELD OF THE INVENTION

The present invention relates to novel intermediates useful in the synthesis of Imiquimod, and the use of said intermediates in a process for its preparation.

TECHNOLOGICAL BACKGROUND

A number of synthetic methods for the preparation of Imiquimod are known, some of which use the corresponding 4-chloro-1H-imidazo[4,5-c]quinoline (I) as an intermediate.

One of these processes is disclosed in U.S. Pat. No. 4,689,338 and can be represented according to the following Scheme 1:

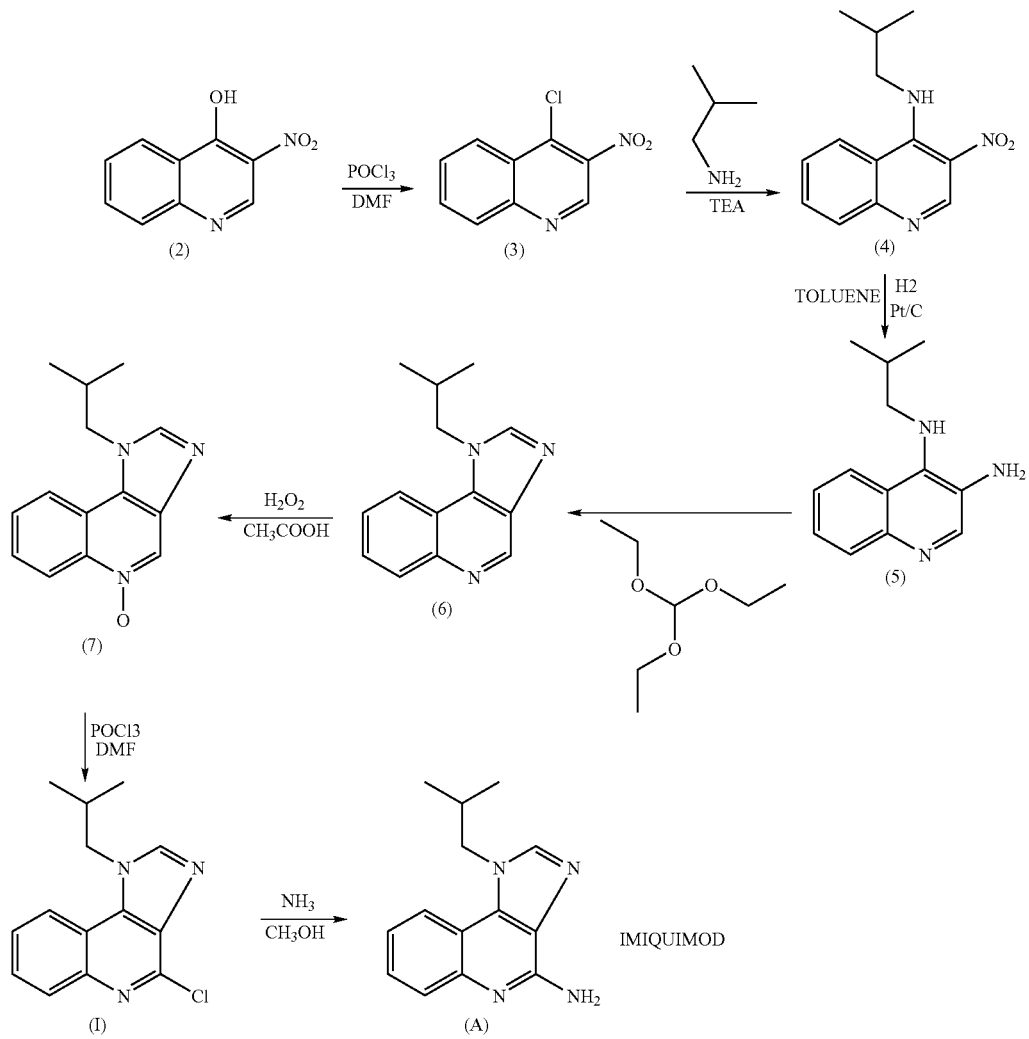

Imiquimod, namely 4-amino-1-isobutyl-1H-imidazo[4,5-c]quinoline (A), is an antiviral, immunomodulating medicament, disclosed in U.S. Pat. No. 4,689,338.

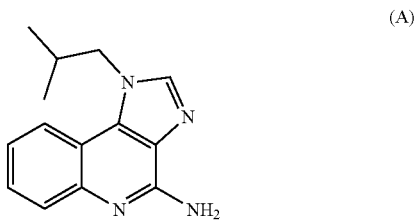

(A)

The synthetic scheme 1 involves, inter alia, the condensation of a quinoline (5), having amino groups at the 3- and 4- positions, with a trialkyl-orthoester to afford the 1H-imidazo[4,5-c]quinoline derivative (6), followed by introduction of a chlorine substituent at the 4-position, previous oxidation of the nitrogen at the 5-position and reaction of the resulting N-oxide (7) with a chlorinated agent. The chlorine atom at the 4-position is then substituted with an amino group by treatment with ammonia. It is apparent from the scheme herein reported that this process is time-consuming and complex. Moreover, the synthesis makes use of nitro derivatives (2), (3) and (4), in addition to the N-oxide (7), which are known to give uncontrollable reactions potentially hazardous to the operators.

The synthesis of Imiquimod via the corresponding 4-chloro-1H-imidazo[4,5-c]quinoline (I) is also disclosed in U.S. Pat. No. 4,988,815, according to the following Scheme 2:

(13) having amino groups at the 3 and 4 positions with a trialkyl-orthoester to afford 4-chloro-1H-imidazo[4,5-c] quinoline (I); and finally the substitution of the chlorine atom at the 4 position with an amino group to give Imiqui-

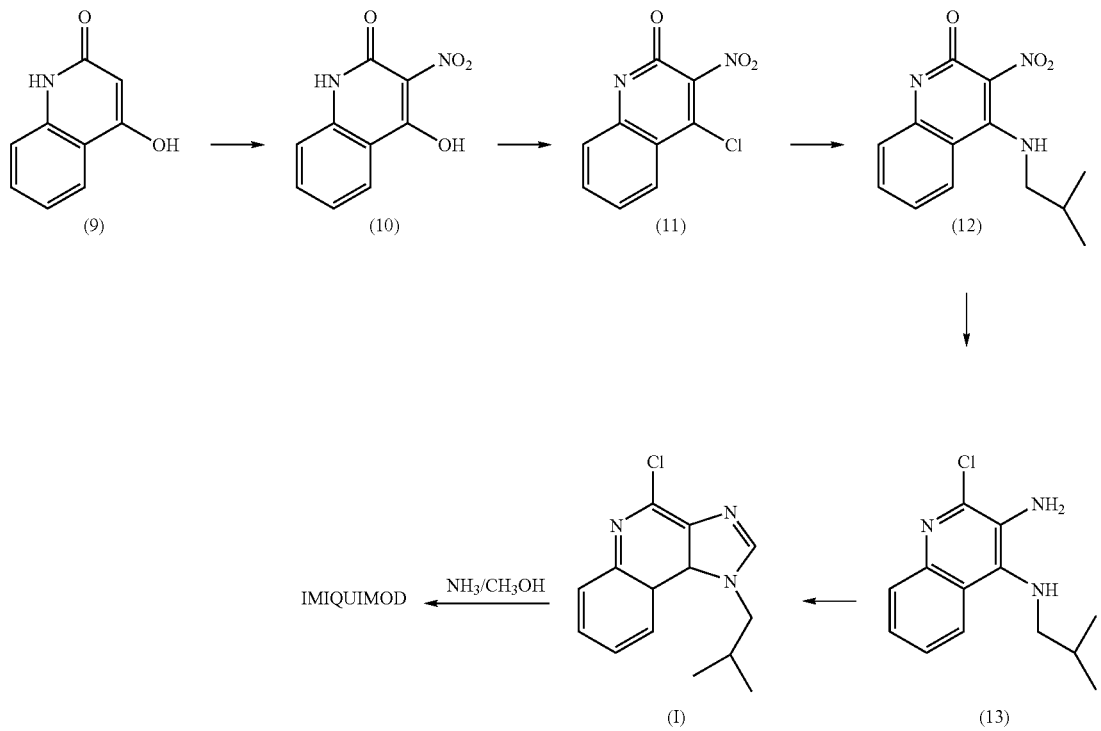

The synthetic Scheme 2 requires, inter alia, the nitration of a compound (9); the introduction of two chlorine atoms at the 2 and 4 positions of a compound (10) to obtain 2,4-dichloro-3-nitroquinoline (11); the amination at the 4 position to give a compound (12); the reduction of the nitro group at the 3 position; the condensation of the quinoline mod. In this case also the process is time-consuming and complex, and the use of nitro derivatives (10), (11) and (12) involves the already mentioned risks. Alternative synthetic routes for the preparation of Imiquimod are reported in WO 97/48704. One of these is represented in the following Scheme 3:

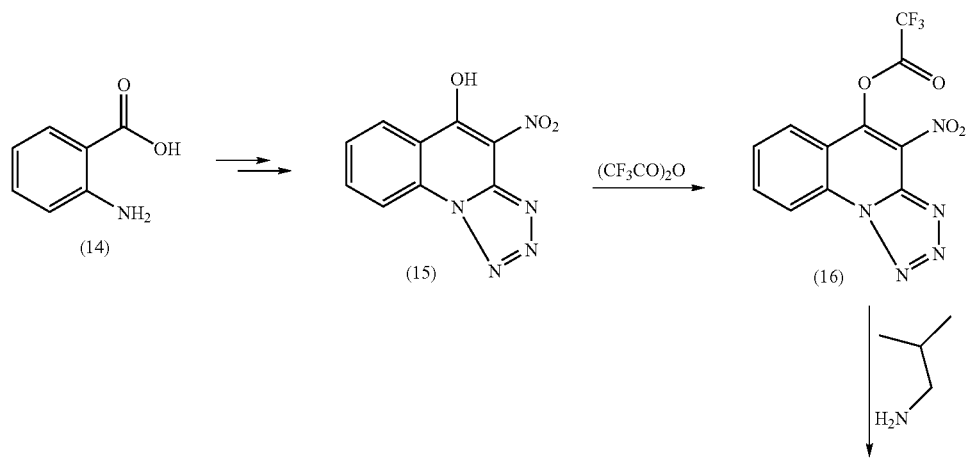

-continued

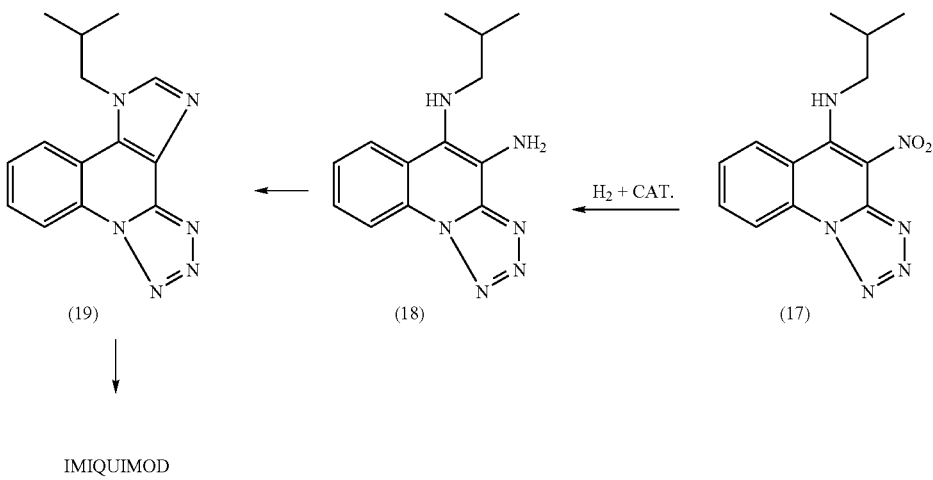

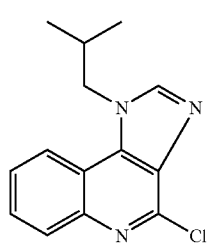

IMIQUIMOD

The process involves the preparation of intermediate (15) which requires, inter alia, the use of nitric acid and sodium azide, products known to be dangerous. Furthermore, said intermediate, like other intermediates useful for the synthesis of Imiquimod, is characterized by the simultaneous presence of a nitro group and a tetrazole ring. These functionalities are known to give the molecule high decomposition energy, which involves risks in handling it. Moreover, these synthetic processes also are long and cumbersome.

There is therefore the need for an alternative process for the preparation of Imiquimod, which is well suited to the industrial production.

It has been found that intermediate (I), described above, can be conveniently obtained with a preparation procedure which is simpler, safer and makes use of commercially available intermediates. The advantages of the novel process for the preparation of Imiquimod, which involve no potentially hazardous intermediates, will be further evidenced in the following.

DETAILED DISCLOSURE OF THE INVENTION

A first object of the invention is a process for the preparation of 1-isobutyl-4-chloro-1H-imidazo[4,5-c]quinoline, of formula (I)

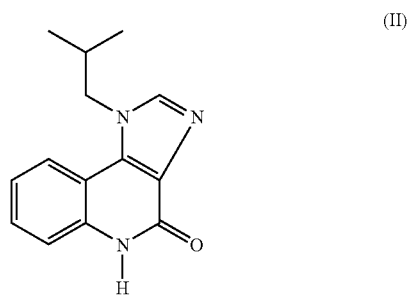

comprising the reaction of 1-isobutyl-1,5-dihydro-imidazo[4,5-a]quinoline-4-one, of formula (II)

(II)

with a chlorinating agent.

A suitable chlorinating agent is, for example, thionyl chloride, sulforyl chloride, phosphorous trichloride, phosphorous pentachloride, phosphorous oxychloride, phosgene and triphosgene, in particular phosphorous oxychloride. The reaction can optionally be carried out in an organic solvent, typically, a chlorinated solvent, such as dichloromethane, dichloroethane, tetrachloroethylene, chlorobenzene or dichlorobenzene; an ester solvent, such as ethyl acetate, isopropyl acetate or butyl acetate; a hydrocarbon solvent, such as cyclohexane, toluene, xylene or mixtures of xylenes; or a mixture of said organic solvents. The chlorinating agent can be used as solvent as well. The reaction can be carried out at a temperature ranging from about 0° C. to the reflux temperature of the reaction mixture, preferably from about 40° C. to the reflux temperature.

The compound of formula (II) is a novel compound and is a further object of the invention, as well as its tautomeric forms, such as the tautomer of formula (IIa),

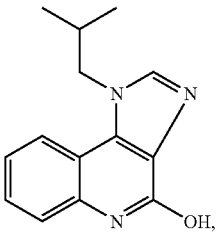

(IIa)

and all the possible isomers thereof.

A compound of formula (II) can be obtained by intramolecular aromatic nucleophilic substitution between the $NH_2$ group and the X group in a compound of formula (III)

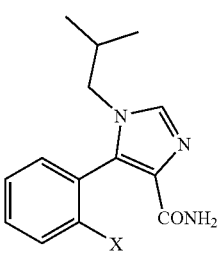

(III)

wherein X is a leaving group.

The leaving group X is preferably a halogen atom, in particular chlorine, bromine or iodine, a nitro group or a reactive hydroxy group, in particular —$OSO_2R$ wherein R is a $C_1$-$C_{10}$ alkyl group, a perchloro or perfluoro $C_1$-$C_{10}$ alkyl group, or an optionally substituted aromatic group, for example phenyl. Preferred examples of X as reactive hydroxy group are mesyloxy, benzenesulfonyloxy, p-toluenesulfonyloxy, p-nitrobenzenesulfonyloxy, trifluoromethylsulfonyloxy and perfluorobutylsulfonyloxy. Particularly preferred meanings of X are bromine and chlorine.

The reaction is preferably carried out in the presence of catalysts, typically based on transition metals, or complexes thereof, such as Pd, Pt and Cu. The Cu based catalysts, particularly cuprous halides such as CuCl, CuBr and CuI, are preferred, the latter being more preferred. Palladium complexes are for example complexes with arylphosphines or aryl-alkylphosphines. The catalyst can be used in the presence of ligands. In the case of copper based catalysts, amino ligands can be used. Diamines, in particular N,N'-dimethylethylenediamine, are preferred.

A compound of formula (III), and all the possible isomers thereof, is a novel compound and is a further object of the invention.

Specific examples of compounds of formula (III) are:

5-(2-bromophenyl)-1-isobutyl-1H-imidazole-4-carboxamide; and 5-(2-chlorophenyl)-1-isobutyl-1H-imidazole-4-carboxamide.

A compound of formula (III) can be obtained by reaction of a compound of formula (IV) with ammonia

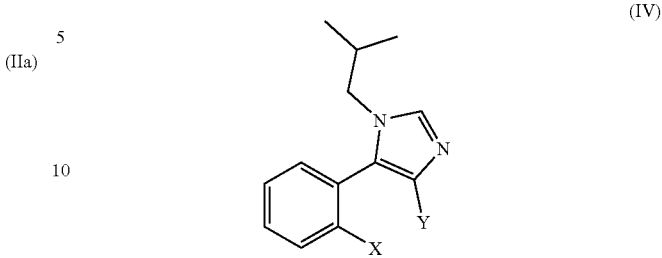

(IV)

wherein X is as defined above and Y is a reactive carboxylic group.

An example of reactive carboxylic group Y is a —CORa group, wherein Ra is a halogen atom, preferably chlorine, or a —COORb group, wherein Rb is a straight or branched $C_1$-$C_{10}$ alkyl group, optionally substituted, or an optionally substituted aryl group, for example phenyl. An Y group can also be a group obtained by activation of the corresponding free carboxylic acid derivative, by treatment with activating agents, for example carbodiimides, such as dicyclohexyl carbodiimide or ethyl dimethylpropyl carbodiimide, carbonyl diimidazole or chloroformates, such as methyl chloroformate, ethyl chloroformate or isobutylchloroformate. Preferably Y is a —CORa or —COORb group, wherein Rb is preferably $C_1$-$C_6$ alkyl, in particular methyl, ethyl or propyl.

The reaction of a compound of formula (IV) with ammonia can be carried out according to known methods, for example as illustrated in the Experimental Section.

A compound of formula (IV) is a novel compound and is a further object of the invention.

Preferred examples of compounds of formula (IV) are:

5-(2-bromophenyl)-1-isobutyl-1H-imidazole-4-chlorocarbonyl;

5-(2-bromophenyl)-1-isobutyl-1H-imidazole-4-carboxylic acid ethyl ester; and 5-(2-chlorophenyl)-1-isobutyl-1H-imidazole-4-carboxylic acid ethyl ester.

A compound of formula (IV) can be obtained according to known methods from the corresponding free carboxylic derivative (V)

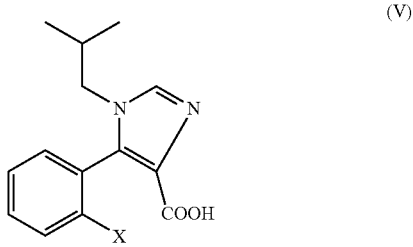

(V)

wherein X is as defined above.

For example, a compound of formula (IV) in which Y is a —CORa group, wherein Ra is a halogen atom, can be obtained by reaction of a compound of formula (V) with a halogenating agent, such as $SOCl_2$, $SO_2Cl_2$, $PCl_3$, $POCl_3$, $PCl_5$, phosgene or triphosgene, according to known methods. A compound of formula (IV) wherein Y is a —COORb group is also a compound of formula (VI) as herein defined and can be obtained following the synthesis described herein.

A compound of formula (V) can be obtained according to the following synthetic Scheme 4, or modifications thereof, by means of known chemical reactions.

Scheme 4

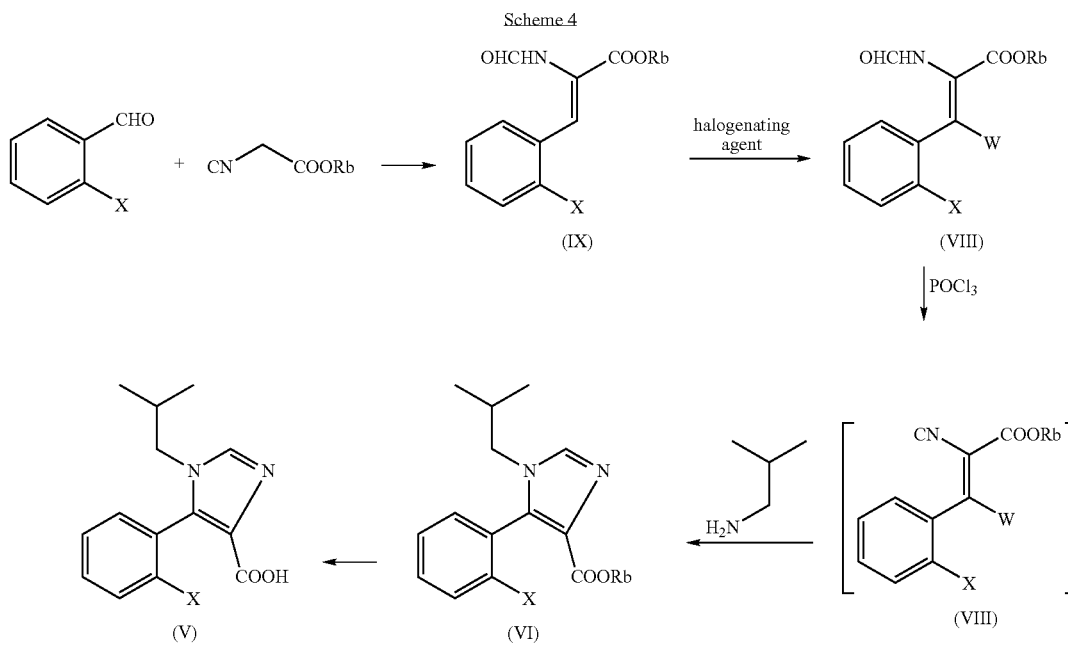

wherein Rb and X are as defined above; W is a halogen atom, such as chlorine or bromine; and the halogenating agent is for example N-chlorosuccinimide or N-bromosuccinimide.

An example of the reactions sequence reported above is illustrated in the Experimental Section. This sequence is preferably carried out using the specific halogenating agents herein indicated and alkyl, in particular ethyl, esters of the compounds of formulae (VI), (VII), (VIII) and (IX). However, this procedure can also be carried out using similar, known methods.

The compounds of formulae (VI), (VII), (VIII) and (IX) above, and the possible isomers thereof, are novel compounds and are a further object of the invention. Preferred compounds of formulae (VI), (VII), (VIII) and (IX) are those in which Rb is $C_1$-$C_6$ alkyl, in particular methyl, ethyl or propyl; W is bromine; and X is bromine or chlorine.

Specific examples of compounds of formula (IX) are:
3-(2-chloro-phenyl)2-formylamino-acrylic acid ethyl ester; and
3-(2-bromo-phenyl)-2-formylamino-acrylic acid ethyl ester.

Specific examples of compounds of formula (VIII) are:
3-bromo-3-(2-bromo-phenyl)-2-formylamino-acrylic acid ethyl ester;
3-bromo-3-(2-chloro-phenyl)-2-formylamino-acrylic acid ethyl ester;
3-chloro-3-(2-bromo-phenyl)-2-formylamino-acrylic acid ethyl ester; and
3-chloro-3 (2-chloro-phenyl)-2-formylamino-acrylic acid ethyl ester.

Specific examples of compounds of formula (VII) are
3-bromo-3-(2-bromophenyl)-2-isocyano-acrylic ethyl acid ester;
3-bromo-3-(2-chlorophenyl)-2-isocyano-acrylic acid ethyl ester;
3-chloro-3-(2-bromophenyl)-2-isocyano-acrylic acid ethyl ester; and
3-chloro-3-(2-chlorophenyl)-2-isocyano-acrylic acid ethyl ester.

Specific examples of compounds of formula (VI) are:
5-(2-bromophenyl)-1-isobutyl-1H-imidazole-4-carboxylic acid ethyl ester; and
5-(2-chlorophenyl)-1-isobutyl-1H-imidazole-4-carboxylic acid ethyl ester.

The invention further provides the use of a compound of formula (II) in a process for the preparation of Imiquimod, more specifically, said process comprising the substitution of the chlorine atom at the 4 position in a compound of formula (I)

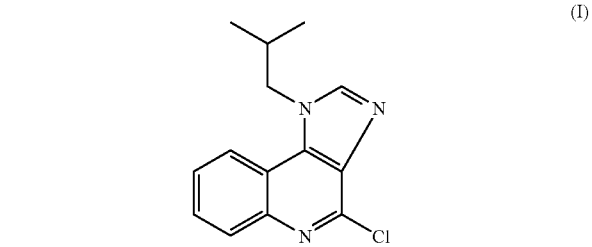

(I)

with an amino group, wherein the compound of formula (I) is obtained by treatment of a compound of formula (II) with a halogenating agent according to the process herein described.

The substitution of the chlorine atom at the 4 position in a compound of formula (I) with an amino group, can be carried out according to known methods, for example as described in U.S. Pat. No. 4,689,338 column 6 or in U.S. Pat. No. 4,988,815 column 4.

The following examples further illustrate the invention.

The $^1$H-NMR spectra were recorded with a Bruker 400 MHz apparatus.

EXAMPLE 1

3-(2-bromo-phenyl)-2-formylamino-acrylic acid ethyl ester; (IX)

A 1M solution of ethyl isocyanoacetate (7.5 ml; 68.6 mM) and 2-bromobenzaldehyde (7.93 ml; 68.6 mM) in anhydrous tetrahydrofuran (THF), is added drop by drop to a suspension of NaH (55-60% in paraffin) (3.60 g; 82.32 mM) in 67 ml of anhydrous THF, the latter on an ice-salt bath (brine). The reaction is carried out at room temperature and is completed in about one hour. The reaction is quenched at 0° C. with a 10% acetic acid solution (67 ml), the organic phase is completely evaporated off and the residue is extracted with $CH_2Cl_2$. The combined organic phases are washed once with water, dried over $Na_2SO_4$, filtered and evaporated under reduced pressure. A crude of 14.5 g (dark brownish oil) is obtained.

The product is crystallized from isopropyl ether thereby obtaining 5.3 g of 3-(2-bromo-phenyl)-2-formylamino-acrylic acid ethyl ester as a white solid.

$^1$H-NMR (CDCl$_3$): δ 1.42 (t, 3H); 4.33-4.44 (q, 2H); 7.07-7.26 (m, 2H); 7.32-7.58 (m, 3H); 7.62-7.69 (bd, 1H); 8.12-8.23 (m, 1H).

According to the same procedure, the following compound can be obtained:

3-(2-chloro-phenyl)-2-formylamino-acrylic acid ethyl ester.

EXAMPLE 2

3-bromo-3-(2-bromo-phenyl)-2-formylamino-acrylic acid ethyl ester; (VIII)

A 0.4 M solution of 3-(2-bromo-phenyl)-2-formylamino-acrylic acid ethyl ester (5.3 g; 17.8 mM) in anhydrous $CH_2Cl_2$, at 0° C., is added with N-bromosuccinimide (3.48 g; 19.6 mM). The mixture is left to slowly warm to room temperature. The reaction is completed in about 5 hours 30 mm. The equivalent amount of triethylamine is added drop by drop; after 30 minutes the mixture is washed with a NaHCO$_3$ saturated solution and then with a NaCl saturated solution. The organic phase is dried over $Na_2SO_4$, the solid is filtered off and the clear solution is evaporated under reduced pressure to a residue. The crude (brownish oil) is purified by flash chromatography, using a 6:4 v/v mixture of hexane and ethyl acetate as eluent, thereby obtaining 2.68 g of 3-bromo-3-(2-bromo-phenyl)-2-formylamino-acrylic acid ethyl ester (white-pale yellow solid). (Yield: 40%).

$^1$H-NMR (DMSO): δ 0.75 (t, 3H); 3.82 (2q, 2H); 7.30-7.36 (m, 2H); 7.43 (t, 1H); 7.67-7.72 (m, 1H); 8.19 (s, 1H); 10.2 (bs, 1H).

According to the same procedure, the following compounds can be obtained:

3-bromo-3-(2-chloro-phenyl)-2-formylamino-acrylic acid ethyl ester;

3-chloro-3-(2-bromo-phenyl)-2-formylamino-acrylic acid ethyl ester; and 3-chloro-3-(2-chloro-phenyl)-2-formylamino-acrylic acid ethyl ester.

EXAMPLE 3

3-Bromo-3-(2-bromophenyl)-2-isocyano acrylic acid ethyl ester; (VII)

A 1M solution of 3-(2bromo-phenyl)-2-formylamino-acrylic acid ethyl ester (2.68 g; 7.11 mM) and triethylamine (2.67 ml; 19.19 mM) in anhydrous $CH_2Cl_2$ is added drop by drop with POCl$_3$ (730 μl, 7.82 mM), under vigorous stirring at −20° C. The mixture is left to slowly warm to room temperature. The reaction is completed after about one hour 15 mm. Quenching is carried out with a 20% solution K$_2$CO$_3$ solution (7.1 ml). The organic phase is washed with water, dried over $Na_2SO_4$, filtered and evaporated under reduced pressure, thereby obtaining 2.55 g of 3-bromo-3-(2-bromophenyl)-2-isocyano-acrylic acid ethyl ester, as crude product (quantitative yield), which is used for the subsequent reaction.

$^1$H-NMR (CDCl$_3$) δ 1.07 (t, 3H); 4.11 (m, 2H); 7.23-7.27 (m, 1H); 7.29-7.31 (m, 1H); 7.40 (m, 1H); 7.64 (dd, 1H $J_1$=8.0 $J_2$=0.8 Hz).

According to the same procedure, the following compounds can be obtained:

3-bromo-3-(2-chlorophenyl)-2-isocyano-acrylic acid ethyl ester;

3-chloro-3-(2-bromophenyl)-2-isocyano-acrylic acid ethyl ester; and 3-chloro-3-(2-chlorophenyl)-2-isocyano-acrylic acid ethyl ester.

EXAMPLE 4

5-(2-Bromophenyl)-1-isobutyl-1H-imidazole-4-carboxylic acid ethyl ester; (VI)

A 0.5 M solution of 3-bromo-3-(2-bromophenyl)-2-isocyano-acrylic acid ethyl ester (2.55 g; 7.11 mM) and triethylamine (990 μl; 7.11 mM) in dimethylformamide (DMF) is added drop by drop at room temperature with isobutylamine (850 μl; 8.53 mM). The reaction mixture is kept at room temperature until complete reaction, then is quenched with a NaHCO$_3$ saturated solution, extracted with ethyl acetate, washed with water, dried over $Na_2SO_4$, and evaporated under reduced pressure. The crude is purified by flash chromatography, eluting with ethyl acetate, to obtain 1.77 g of 5-(2-bromophenyl)-1-isobutyl-1H-imidazole-4-carboxylic acid ethyl ester. (Yield: 71%).

$^1$H-NMR (CDCl$_3$) δ 0.80 (d, 3H); 0.84 (d, 3H); 1.21 (t, 3H); 1.83 (m, 1H); 3.47 (q, 1H); 3.65 (q, 1H); 4.23 (m, 2H); 7.29-7.39 (m, 2H); 7.40-7.46 (m, 1H); 7.59 (s, 1H); 7.72 (bd, 1H).

According to the same procedure, the following compound can be obtained:

5-(2-chlorophenyl)-1-isobutyl-1H-imidazole-4-carboxylic acid ethyl ester.

EXAMPLE 5

5-(2-Bromophenyl)-1-isobutyl-1H-imidazole-4-carboxylic acid; (V)

A 0.2 M solution of 5-(2-bromophenyl)-1-isobutyl-1H-imidazole-4-carboxylic acid ethyl ester (1.77 g; 5.04 mM) in 1/1 v/v methanol/water is added with NaOH (605 mg; 15.12 mM). The mixture is kept at room temperature for about 15 hours, then acidified with KHSO$_4$, extracted with ethyl acetate, dried over $Na_2SO_4$, filtered and evaporated under reduced pressure, thereby obtaining 1.42 g of 5-(2-bromophenyl)-1-isobutyl-1H-imidazole-4-carboxylic acid, as a white-pale yellow solid which is used in the subsequent reaction without further purification. (Yield: 87%).

According to the same procedure, the following compound can be obtained:

5-(2-chlorophenyl)-1-isobutyl-1H-imidazole-4-carboxylic acid.

EXAMPLE 6

5-(2-Bromophenyl)-1-isobutyl-1H-imidazole-4-carboxamide; (III)

A 0.2 M solution of 5-(2-bromophenyl)-1-isobutyl-1H-imidazole-4-carboxylic acid (1.42 g; 4.4 mM) in anhydrous THF is added drop by drop, at 0° C., with oxalyl chloride (376 µl; 4.4 mM), then left to react at room temperature for about one hour, thus obtaining 5-(2-bromophenyl)-1-isobutyl-1H-imidazole-4-chlorocarbonyl. The mixture is then added drop by drop with 3 ml of conc. NH₃ and reacted for one hour, then extracted with ethyl acetate, dried over Na₂SO₄, filtered and evaporated under reduced pressure, thereby obtaining 1.14 g of 5-(2-bromophenyl)-1-isobutyl-1H-imidazole-4-carboxamide which is used directly in the subsequent reaction. (Yield: 80.5%).

$^1$H-NMR (CDCl₃) δ 0.79 (d, 3H); 0.84 (d, 3H); 1.82 (m, 1H); 3.48 (q, 1H); 3.66 (q, 1H); 5.30-5.37 (bs, 1H); 7.11-7.18 (bs, 1H); 7.32-7.38 (m, 2H); 7.41-7.46 (m, 1H); 7.65 (bs, 1H); 7.69-7.73 (m, 1H).

According to the same procedure, the following compound can be obtained:

5-(2-chlorophenyl)-1-isobutyl-1H-imidazole-4-carboxamide.

EXAMPLE 7

1-Isobutyl-1,5-dihydro-imidazo[4,5-a]quinoline-4-one; (II)

5-(2-Bromophenyl)-1-isobutyl-1H-imidazole-4-carboxamide (1.14 g; 3.54 mM), CuI (134.8 mg) and potassium carbonate (978 mg; 7.08 mM) are placed in a round-bottom flask under N₂ for about 15 minutes, then 35.4 ml of anhydrous toluene and N,N'-dimethylethylenediamine (45 µl) are added and the mixture is refluxed at 110° C. under nitrogen atmosphere. After 48 h the solvent is evaporated off under reduced pressure and the mixture is purified by flash chromatography, eluting with ethyl acetate/methanol in 75/25 v/v ratio, thereby obtaining 307 mg of 1-isobutyl-1,5-dihydro-imidazo[4,5-a]quinoline-4-one. (Yield: 36%).

$^1$H-NMR (CDCl₃) δ 0.91 (d, 6H); 2.12 (m, 1H); 4.38 (d, 2H); 7.25-7.31 (m, 1H); 7.43-7.50 (m, 2H); 7.95 (d, 1H); 8.14 (bs, 1H); 11.60 (bs, 1H).

EXAMPLE 8

1-Isobutyl-4-chloro-1H-imidazo[4,5-c]quinoline; (I)

A solution of 1-isobutyl-1,5-dihydro-imidazo[4,5-a] quinoline-4-one (307 mg; 1.18 mM) in POCl₃ (1 ml) is refluxed for about one hour 30 min., then quenched with ice-water, alkalinised by dropwise addition of conc. NH₄OH and extracted with ethyl acetate. The organic phase is dried over Na₂SO₄, filtered and evaporated under reduced pressure. The crude is purified by flash chromatography, eluting with ethyl acetate, thereby obtaining 90 mg of 1-isobutyl-4-chloro-1H-imidazo[4,5-c]quinoline. (Yield: 30%).

$^1$H-NMR (CDCl₃) δ 1.08 (d, 6H); 2.37-2.43 (m, 1H); 4.41 (d, 2H); 7.73 (ddd, 1H, J₁=7.0 J₂=8.5 J₃=1.5 Hz); 7.68 (ddd, 1H, J₁=7.0 J₂=8.3 J₃=1.3 Hz); 8.09-8.13 (m, 2H); 8.22-8.27 (m, 1H).

The invention claimed is:

1. A process for the preparation of Imiquimod (A):

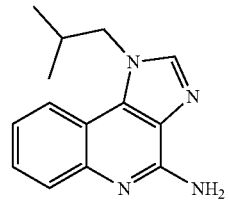

comprising:

treating a compound of formula (III)

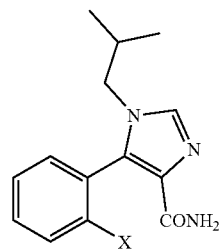

wherein X is a leaving group;

to an intramolecular aromatic nucleophilic substitution between the NH₂ group and the X group to give a compound of formula (II)

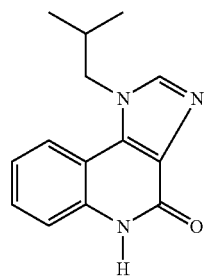

reacting the compound of formula (II) with a chlorinating agent to give a compound of formula (I)

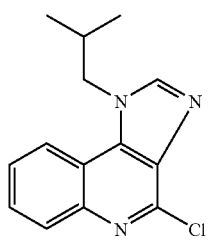

and thereafter substituting the chlorine atom at position 4 with an amino group.

2. The process according to claim 1, wherein the chlorinating agent is selected from the group consisting of thionyl chloride, sulforyl chloride, phosphorous trichloride, phosphorous pentachloride, phosphorous oxychloride, phosgene and triphosgene.

3. The process according to claim 1, wherein the leaving group X is selected from the group consisting of a halogen atom, a nitro group and a reactive hydroxy group, and the intramolecular aromatic nucleophilic substitution is carried out in the presence of transition metal based catalysts, or complexes thereof.

4. The process according to claim 3, wherein the catalyst is a cuprous halide.

5. The process according to claim 2, wherein the leaving group X is selected from the group consisting of a halogen atom, a nitro group and a reactive hydroxy group, and the intramolecular aromatic nucleophilic substitution is carried out in the presence of transition metal based catalysts, or complexes thereof.

6. The process according to claim 5, wherein the catalyst is a cuprous halide.

* * * * *